US007766837B2

(12) United States Patent
Pedrizzetti et al.

(10) Patent No.: US 7,766,837 B2
(45) Date of Patent: Aug. 3, 2010

(54) M-TRACKING FOR SPACE-TIME IMAGE

(75) Inventors: Gianni Pedrizzetti, Prato (IT); Emidio Marchese, Popoli (IT); Giovanni Tonti, Sulmona (IT)

(73) Assignee: Esaote S.p.A., Milan (IT)

( * ) Notice: Subject to any disclaimer, the term of this patent is extended or adjusted under 35 U.S.C. 154(b) by 732 days.

(21) Appl. No.: 10/506,052

(22) PCT Filed: Feb. 27, 2002

(86) PCT No.: PCT/IT02/00114

§ 371 (c)(1),
(2), (4) Date: Jan. 18, 2005

(87) PCT Pub. No.: WO03/071950

PCT Pub. Date: Sep. 4, 2003

(65) Prior Publication Data

US 2005/0119553 A1    Jun. 2, 2005

(51) Int. Cl.
*A61B 8/06* (2006.01)
(52) U.S. Cl. .................. 600/451; 600/453; 600/454; 600/455; 382/128; 382/130; 382/131; 382/132
(58) Field of Classification Search .............. 600/451, 600/453, 455
See application file for complete search history.

(56) References Cited

U.S. PATENT DOCUMENTS

| | | | | |
|---|---|---|---|---|
| 4,660,564 A | * | 4/1987 | Benthin et al. | 600/449 |
| 5,097,836 A | * | 3/1992 | Yamada et al. | 600/443 |
| 5,195,525 A | * | 3/1993 | Pelc | 600/410 |
| 5,322,067 A | * | 6/1994 | Prater et al. | 600/443 |
| 5,355,887 A | * | 10/1994 | Iizuka et al. | 600/440 |
| 5,474,070 A | * | 12/1995 | Ophir et al. | 600/437 |
| 5,515,856 A | * | 5/1996 | Olstad et al. | 600/440 |
| 5,568,811 A | * | 10/1996 | Olstad | 600/443 |
| 5,568,812 A | * | 10/1996 | Murashita et al. | 600/440 |
| 5,579,771 A | * | 12/1996 | Bonnefous | 600/450 |
| 5,615,680 A | | 4/1997 | Sano | |
| 5,701,897 A | * | 12/1997 | Sano | 600/453 |
| 5,800,356 A | | 9/1998 | Criton et al. | |

(Continued)

OTHER PUBLICATIONS

Kanai, H. et al., "Noninvasive Evaluation of Local Myocardial Thickening and Its Color-Coded Imaging", IEEE Transactions of Ultrasonics, Ferroelectrics and Frequency Control, IEEE Inc., New York, vol. 44, No. 4, Jul. 1, 1997, pp. 752-768.

(Continued)

*Primary Examiner*—Brian Casler
*Assistant Examiner*—Baisakhi Roy
(74) *Attorney, Agent, or Firm*—Woodard, Emhardt, Moriarty, McNett & Henry LLP

(57) ABSTRACT

A new method is introduced able to track the motion of a thin object, e.g. a wall, from a series of digital field data (e.g. images) in order to analyze field information corresponding to the moving position of the object. The method is based on the extraction of M-mode images where the wall can be identified and the wall properties can be extracted and analyzed. The digital implementation of the method into electronic equipments improves the quality of the information that can be extracted from field data and the potential diagnostic capability when applied to echographic medical imaging.

8 Claims, 5 Drawing Sheets

Example of one image of the left ventricle acquired during diagnostic evaluation of myocardial perfusion.

U.S. PATENT DOCUMENTS

| | | | |
|---|---|---|---|
| 5,820,561 A * | 10/1998 | Olstad et al. | 600/453 |
| 5,840,028 A * | 11/1998 | Chubachi et al. | 600/437 |
| 6,106,465 A * | 8/2000 | Napolitano et al. | 600/443 |
| 6,174,287 B1 * | 1/2001 | Resnick et al. | 600/458 |
| 6,267,728 B1 | 7/2001 | Hayden | |
| 6,352,507 B1 * | 3/2002 | Torp et al. | 600/438 |
| 6,537,221 B2 * | 3/2003 | Criton et al. | 600/454 |
| 6,579,240 B2 * | 6/2003 | Bjaerum et al. | 600/447 |
| 6,638,221 B2 * | 10/2003 | Abe et al. | 600/437 |
| 6,692,438 B2 * | 2/2004 | Skyba et al. | 600/440 |
| 6,884,216 B2 * | 4/2005 | Abe et al. | 600/440 |
| 6,909,914 B2 * | 6/2005 | Pedrizzetti et al. | 600/407 |
| 6,976,961 B2 * | 12/2005 | Jackson et al. | 600/443 |
| 6,994,673 B2 * | 2/2006 | Lysyansky et al. | 600/443 |
| 7,343,031 B2 * | 3/2008 | Pedrizzetti et al. | 382/128 |
| 2008/0095417 A1 * | 4/2008 | Pedrizzetti et al. | 382/128 |
| 2008/0118109 A1 * | 5/2008 | Pedrizzetti et al. | 382/103 |

OTHER PUBLICATIONS

Kenai, H. et al., "Realtime Velocimetry for Evaluation of Change in Thickness of Myocardium and Arterial Wall", 1998 IEEE Ultrasonics Symposium Proceedings, vol. 2, Oct. 5, 1998, pp. 1365-1368.

* cited by examiner

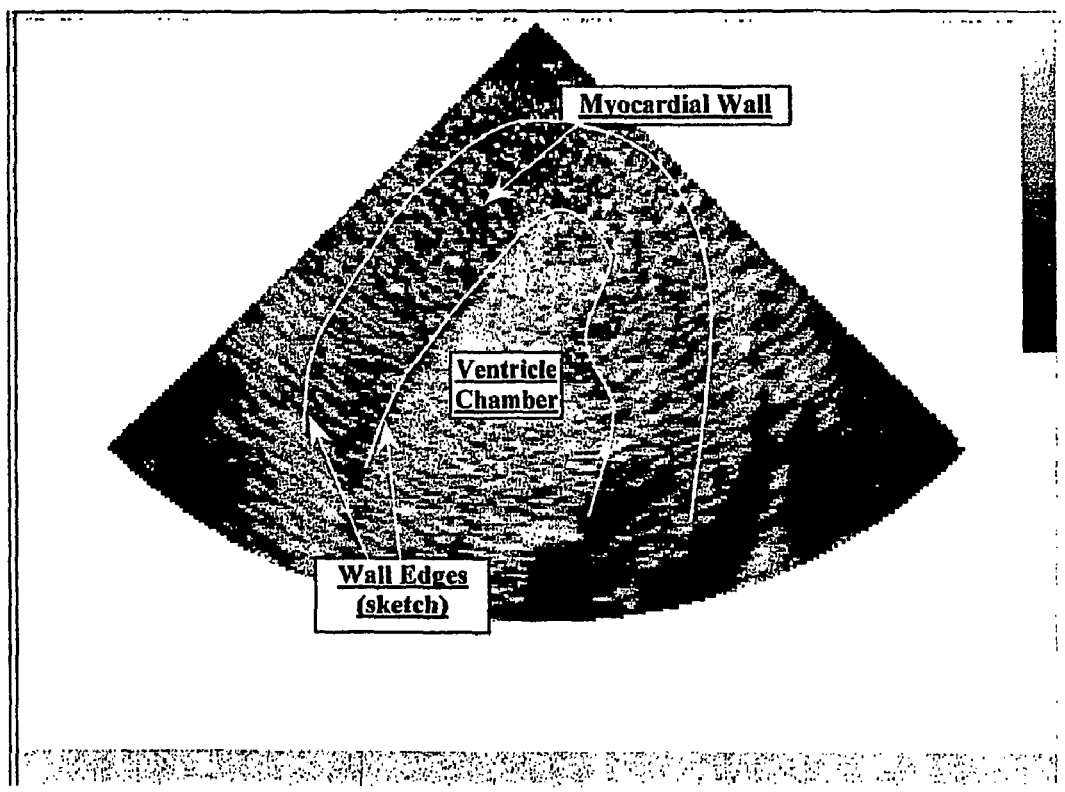
*Figure 1. Example of one image of the left ventricle acquired during diagnostic evaluation of myocardial perfusion.*

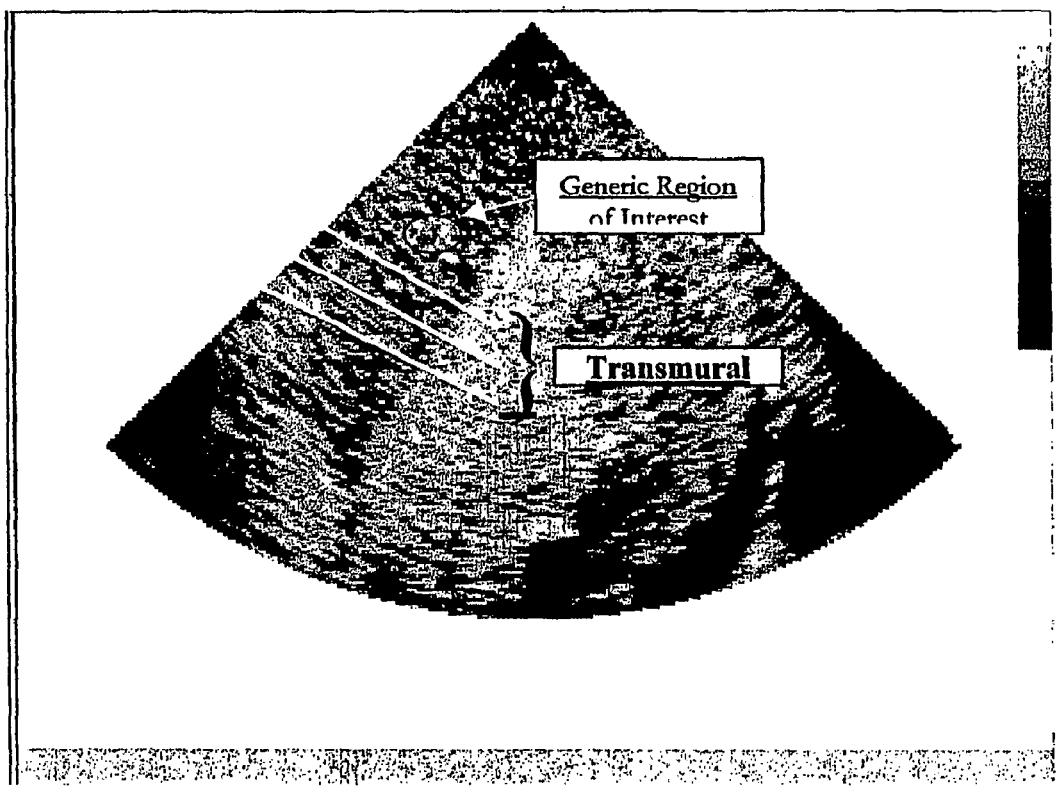
Figure 2. Drawing of segments that cross the wall over all its thickness (the trasmural cuts employed in the new method), and a generic region of interest that instantaneously falls over the wall.

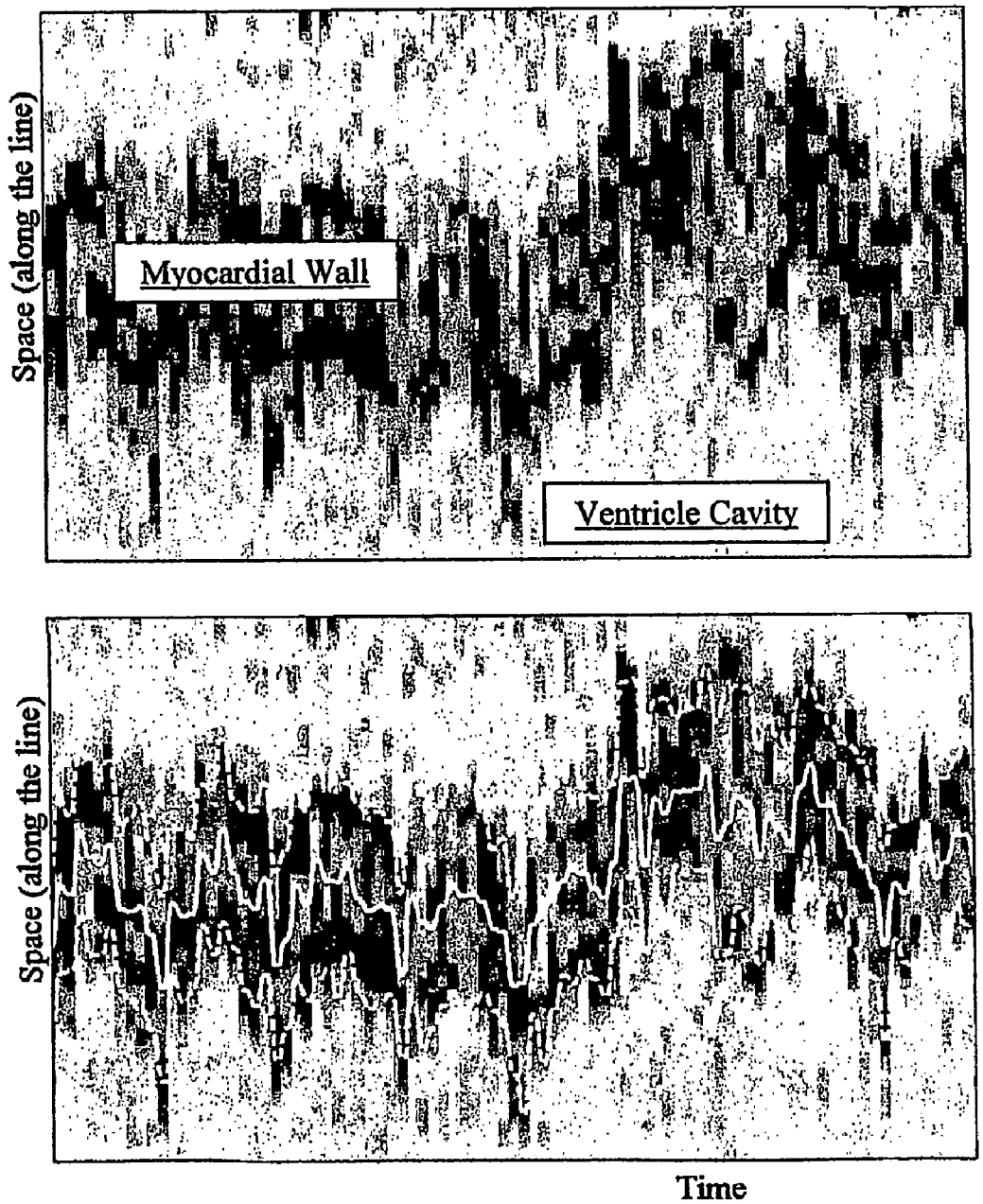
Figure 3. M-mode representation of the time evolution of the brightness along one line crossing the myocardial wall. The M-mode only (above), and (below) the M-mode with the darkness center (continuous line) and thickness (dashed lines) plotted superimposed as automatically recognized by statistical methods.

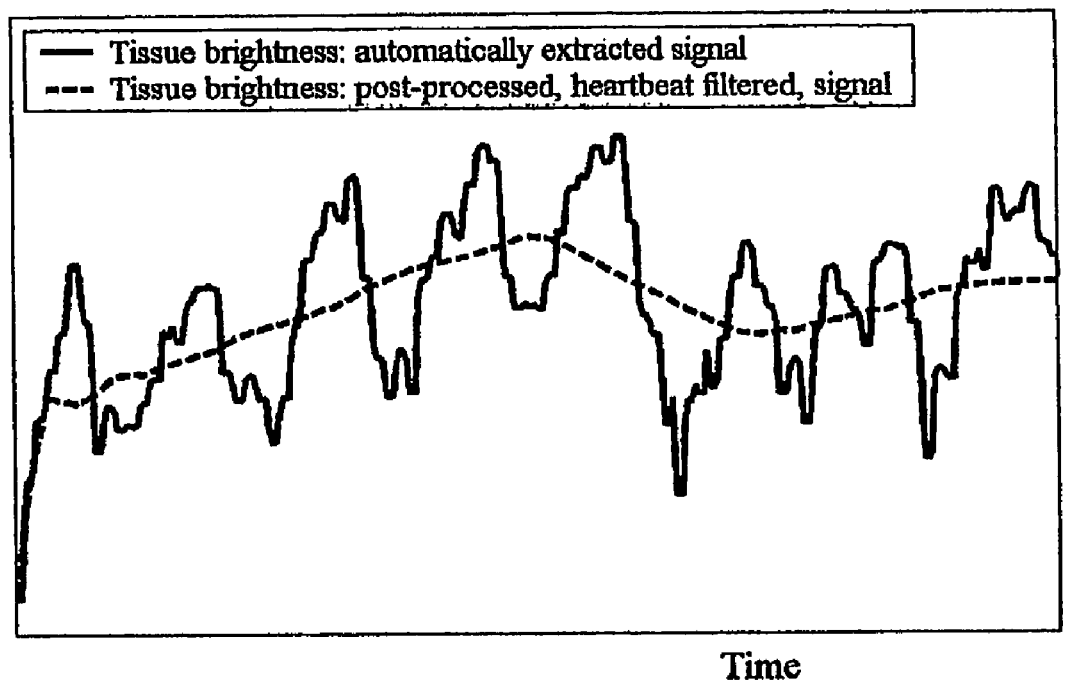
Figure 4. Example of the time evolution of the myocardial brightness as evaluated automatically (from data in figure 3) in correspondence of the tracked myocardial region.

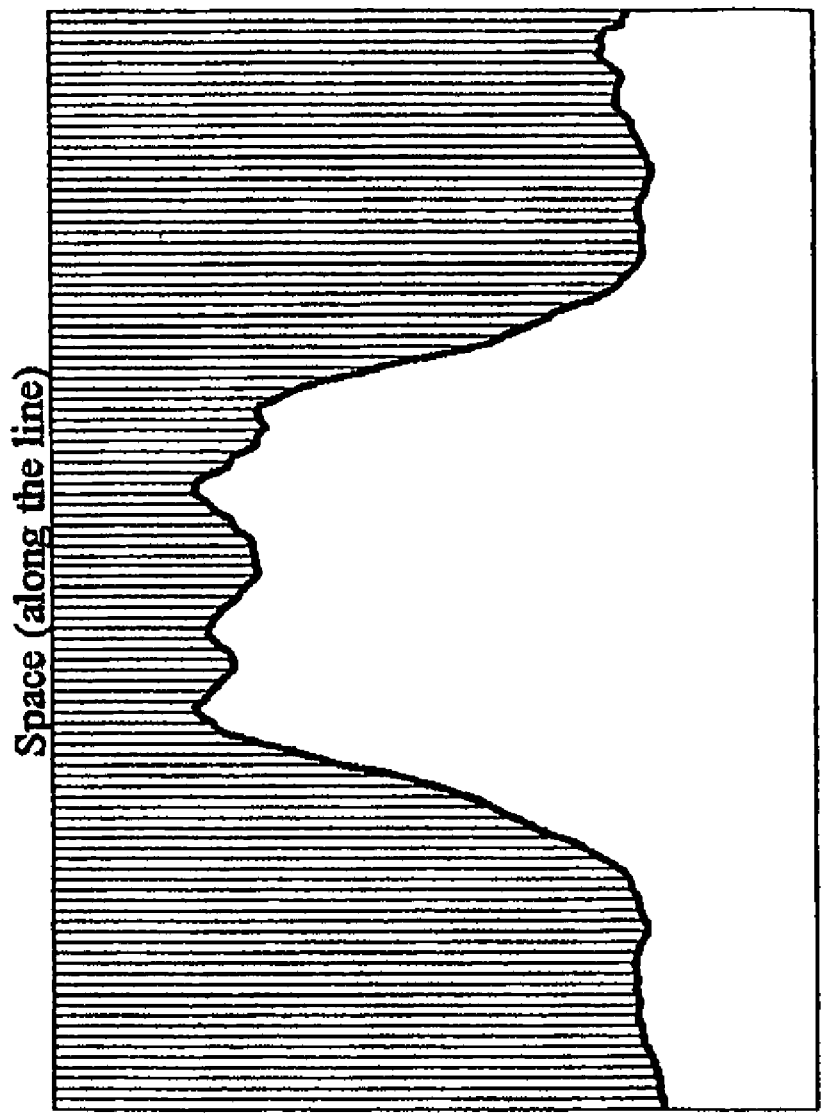
*Figure 5. Example of the time-averaged myocardial brightness as evaluated automatically (from data in figure 3) keeping the alignment at each instant of the tracked myocardial region.*

M-TRACKING FOR SPACE-TIME IMAGE

TECHNICAL FIELD

Automatic processing of two- and three-dimensional time-varying digital data analysis, primarily pertinent to medical imaging (e.g. echographic images) to improve the ability of extracting specific tissue-related information.

BACKGROUND ART

In many practical, clinical and industrial, applications it is often requested the evaluation of properties in correspondence of a specific element of a system and the quantification of the variation of such properties with time. The application that stimulated the development of the present method derives from capability of tracking the moving vascular wall (e.g. myocardium) from cardiovascular images in such a way to extract from the image the properties (velocity, brightness, etc.) evaluated in correspondence of the tissue.

One driving example is the analysis of the time-course of blood flow in the capillary bed of the myocardium, based on the echo-contrast imaging. The health of the myocardium can be established, among other ways, from the ability of the blood to reach all muscular cells; if a myocardial region is not perfused then derives mechanical failure (e.g. during angina or myocardial infarction). It is therefore important to develop techniques able to evaluate the perfusion properties of the different tissue regions. The quantification of myocardial perfusion is made by introducing a contrast agent in vein, it moves with the blood and quantification of its presence in the myocardial tissue is equivalent to quantification of myocardial perfusion (Becher and Burns 2000). The analysis is made utilizing the ability of ultrasound machine to detect the echo enhancement deriving from the contrast medium that perfuses the myocardium. Recent examples of quantitative analysis of segmental perfusion are reported in literature (Nor-Avi et al. 1993; Wei et al. 1998; Masugata et al. 2001).

Crucial for an adequate quantification of the contrast signal is the ability to follow the systolic and diastolic movement of the heart walls. With the respect of the ultrasound probe, the heart show not only inherent movement but also displacements due to respiration. Moreover, the physician performing the examination can move the probe itself during the acquisition of the data. For these reasons, if we try to register the signal of the wall utilizing a region of interest (ROI) placed at a fixed location, frequently, the ROI fall on other structures (like left or the right ventricular cavities or outside the heart). For these reasons, only if the wall is continuously tracked we can extract the signal originating from the tissue and not outside of it and so extract quantitative parameters of regional perfusion.

Such an approach has a widespread application not only in echocardiography (e.g perfusion study analysis, regional wall velocity analysis and quantification, computation of segmental strain and strain rate (Heimdal et al. 1998; Voigt et al. 2000)) but also in industrial applications when the tracking of a moving material is necessary and in some applications of visual recognition by intelligent electronic devices.

Currently, the quantification of wall-related properties is performed simply by analyzing the properties within a ROI, (sometimes just a few pixels within the image) selected well inside the myocardial tissue. It is then important to verify that the selected ROI remains inside the tissue in all the images of the sequence otherwise information that do not pertain to the tissue are included and the analysis is corrupted. To make sure that we aren't introducing erroneous samples in the dataset, the sequence should be reviewed frame by frame: when the ROI falls outside the tissue it must be moved manually on the wall. It is evident how such an approach is inherently extremely time-consuming (in most case for each ROI we must review more than 100 frames and a compete evaluation requires to analyze up to 20 different ROI). Sometimes this procedure can performed automatically with methods that depend from the software available. In most cases, these are based on standard edge detection algorithm or on cross-correlation alignment methods (Pratt 1991), however these technique do not guarantee the accuracy of the results that must be still verified manually because they incorporate no information about the structure and the geometry, of the object that must be recognized.

We present here a novel method that allows to continuously tracks in time the wall contained inside a two or three-dimensional representation (images) that is well suited for the case when the wall is relatively thin. After the wall is recognized it is straightforward to analyze the time evolution of properties in correspondence of the detected wall.

DISCLOSURE OF THE INVENTION

Consider a two-dimensional image containing a non-uniform elongated region corresponding to the part of the tissue that we want to analyze. One example in reported in FIG. 1 where an image of the left ventricle is show as taken from echographic machine during contrast analysis. The wall is not immediately recognizable as a well-defined structure separated from the background; nevertheless it is possible to evaluate properties (e.g. brightness of the image that is proportional to the amount of contrast inside the myocardium, in the example of FIG. 1) in correspondence of the tissue.

It is common practice to select a region that is instantaneously over the wall (FIG. 2), and to control in the following images if it remains over it. Differently an automatic procedure can be developed as follows.

Consider one segment (or a series of them), that crosses the wall along the whole thickness, i.e. a transmural cut, being sure that the segment is long enough and starts and ends outside the wall during all instants as shown in the image of FIG. 2. The distribution of the sought property (e.g. brightness) along the single line can be represented for all instants at once in a two-dimensional representation (often referred as M-mode representation) where one axis is the distance along the line and the other axis is the time. An example of such a representation is shown in FIG. 3 (above).

Once a M-mode representation is obtained the matter of defining the wall becomes substantially facilitated. In fact the wall should now be sought, at each instant, simply along a single line, where its center is defined by one single point and the wall edge (in those cases when an edge can be defined) is defined by two points as shown in FIG. 3 (below). The center of the wall can be defined with statistical methods by the center of the distribution of the brightness or darkness (or another desired quantity in different applications). The wall thickness can be sought by standard one-dimensional edge finding methods or, statistically, by the dispersion of the wall related property.

This method for tissue tracking is easily translated into an automatic procedure to be included into a software application for analysis of tissue-related properties:

1. Consider a sequence of N digital images, read from a storage medium, made of a number M of pixels (i.e. M is the product of the number of rows and of columns in structured images), and each image contains one datum for one specific quantity (e.g. brightness in contrast echography, velocity in Doppler images) such that q(i,k) is the digital value of such a quantity in the $i^{th}$ pixel of the $k^{th}$ image;

2. The manual drawing of a line (or a curve) over one image corresponds to selecting a group of M' pixels inside the images, whose indexes can be identified by one integer array ig of dimension M';

3. The M-mode representation is a new single array qm of dimension M'☐N such that qm(i,k)=q(ig(i),k);

4. The sought tissue properties are evaluated at the $k^{th}$ instant by analysing the single value function qm( . . . ,k) from which it is straightforward to extract any properly defined quantity with methods taken from statistical analysis, specific weighted integrals, or from one dimensional edge detection techniques.

Results can also be averaged from a series of M-modes in order to analyze a finite segment of tissue.

Different examples of the potential outputs are:

a Define the tissue center (e.g. function barycentre) and its thickness (e.g. function standard deviation), and evaluate the time evolution of the property value integrated over the tissue thickness. One example of this application is shown in FIG. 4.

b. The unbiased time-averaged spatial profile of the tissue property can be evaluated, after a tissue center is defined, by performing averages keeping the center of tissue aligned during time. One example of this application is shown in FIG. 5.

The accuracy of this method is inherently related to the quality of the image itself, nevertheless this new approach is optimal in the case of noisy images, like the ones shown in the figures, because transforms the two- or three-dimensional problem into a series of one-dimensional ones. The three-dimensional case does not differ conceptually from the two-dimensional one although its software implementations includes more complex management steps based on voxels in place of pixels.

This method can be inserted into software applications for different specific purposes to improve the accuracy of analysis concerning tissue related properties. The routine for wall tracking has been included into two different sofware applications for myocardial perfusion and for tissue strain analysis. Different versions of these software, with different language implementations, have been prepared to run on personal computers where digital images, read from echographs, are available. The software has been extensively tested in a series of applications about Tissue Doppler analysis and cardiac echo-contrast experiments with clinical cases to verify its applicability. The results confirm the physical consistency and accuracy of the method.

BEST MODE FOR CARRYING OUT THE INVENTION

The procedure resulting from the serial combination of the passages outlined above is a method that allows to identify the wall, or another inhomogeneous region, on the basis of the normal data measured from echographs and commonly represented as image. Implementation of this technique must be based on a numerical analysis (software application), therefore it should be supported in digital processing by an electronic instrument.

The procedure outlined above can be implemented with most programming languages, and the routine included inside a complete software application for the analysis of tissue related properties. The software can be an internal one running on echographic machines or can be executed on an external computer equipped to read the echographic data.

The direct inclusion into echographs is more appropriate in the case of an application for rapid analyses that can be performed during the normal echograph use. The inclusion into an external device is more appropriate in the case of software dedicated to more accurate analysis that are commonly performed offline. In both cases the equipment becomes a system with the capability of automatic wall recognition and is able to evaluate the wall-related properties thus minimizing the risk of taking data that do not compete to the tissue.

The implementation of the new approach improves the quality of the information that can be obtained from the electronic equipment, thus giving an additional potential feature that is potentially relevant for several diagnostic applications.

CITED REFERENCES

1. H. Becher and P. Burns, *Handbook of Contrast Echocardiography: Left Ventricular Function and Myocardial Perfusion*. Springer, 2000.
2. A. Heimdal, A. Støylen, H. Torp, T. Skjærpe, "Real-Time Strain Rate Imaging of the Left Ventricle by Ultrasound", *J Am Soc Echocardiogr* vol. 11 pp. 1013-9, 1998.
3. H. Masugata, B. Peters, S. Lafitte, G. M. Strachan, K. Ohmori, A. N. DeMaria, "Quantitative assessment of myocardial perfusion during graded coronary stenosis by real-time myocardial contrast echo refilling curves", *J Am Coll Cardiol*, vol. 37, pp. 262-9, 2001.
4. V. Mor-Avi, D. David, S. Akselrod, Y. Bitton, I. Choshniak, "Myocardial regional blood flow: quantitative measurement by computer analysis of contrast enhanced echocardiographic images", *Ultrasound Med Biol* vol. 19 pp. 619-33, 1993.
5. W. K. Pratt, *Digital Image Processing,* 2nd edition. Wiley, 1991.
6. J.-U. Voigt, M. F. Arnold, M. Karlsson, L. Hübbert, T. Kukulski, L. Hatle, G. R. Sutherland, "Assessment of Regional Longitudinal Myocardial Strain Rate Derived from Doppler Myocardial Imaging Indexes in Normal and Infarcted Myocardium", *J Am Soc Echocardiogr* vol. 13 pp. 588-98, 2000.
K. Wei, A. R. Jayaweera, S. Firoozan, A. Linka, D. M. Skyba, S. Kaul, "Quantification of myocardial blood flow with ultrasound-induced destruction of microbubbles administered as a constant venous infusion", *Circulation* vol. 97 pp. 473-83, 1998.

The invention claimed is:

1. A method for evaluating a property of a moving tissue region characterized by the steps of:
   scanning a series of transmural cuts crossing said tissue region and constructing corresponding space-time images of said transmural cuts;
   analyzing each of said space-time images to form information of said tissue moving along said transmural cuts;
   extracting property from said information corresponding to said moving tissue;
   averaging the results of said extracting to reconstruct said property for said moving tissue region; and
   visually depicting said reconstruction of said property for said moving tissue region.

2. A method as claimed in claim 1, applied to a sequence of three-dimensional sets of data.

3. A method as claimed in claim 1, applied to medical Tissue Doppler Imaging.

4. A method as claimed in claim 1 applied to non medical imaging that requires representation of a non-uniform elongated moving region.

5. A method for evaluating a time-average representation of a property of a moving tissue region characterized by the steps of:

scanning a series of transmural cuts crossing said tissue region and constructing corresponding space-time images of said transmural cuts;

analyzing each of said space-time images to form information of said tissue moving along said transmural cuts;

aligning said space-time images to eliminate or reduce the appearance of tissue motion;

assigning said aligned space-time images to appropriate pixel values along said transmural cuts;

combining said pixel values for each of said transmural cuts to obtain a representation of said moving tissue region; and visually depicting said information and said representation of said moving tissue region.

6. A method as claimed in claim 5, applied to a sequence of three-dimensional sets of data.

7. A method as claimed in claim 5, applied to medical Tissue Doppler Imaging.

8. A method as claimed in claim 5 applied to non medical imaging that requires representation of a non-uniform elongated moving region.

\* \* \* \* \*